United States Patent
Lewis

(10) Patent No.: US 8,753,696 B1
(45) Date of Patent: Jun. 17, 2014

(54) METHODS FOR PREPARING CANNABIS AND RELATED PRODUCTS

(71) Applicant: David Lewis, Moorpark, CA (US)

(72) Inventor: David Lewis, Moorpark, CA (US)

( * ) Notice: Subject to any disclaimer, the term of this patent is extended or adjusted under 35 U.S.C. 154(b) by 0 days.

(21) Appl. No.: 13/652,609

(22) Filed: Oct. 16, 2012

(51) Int. Cl.
*A01N 65/00* (2009.01)

(52) U.S. Cl.
USPC ............................................ 424/725

(58) Field of Classification Search
None
See application file for complete search history.

(56) References Cited

U.S. PATENT DOCUMENTS

2013/0078296 A1* 3/2013 Grlica et al. ................. 424/405

* cited by examiner

*Primary Examiner* — Michael Meller
(74) *Attorney, Agent, or Firm* — Plager Schack LLP

(57) ABSTRACT

A method for preparing a medical marijuana mixture includes combining prepared medical marijuana and an alkaline substance in a pulverizing device. The alkaline substance may be coconut, cinnamon, or the like. The pulverizing device may be a coffee grinder, a food processor, a blender, or the like. The mixture may optionally include a sweetener, such as sugar, stevia, or the like.

2 Claims, 1 Drawing Sheet

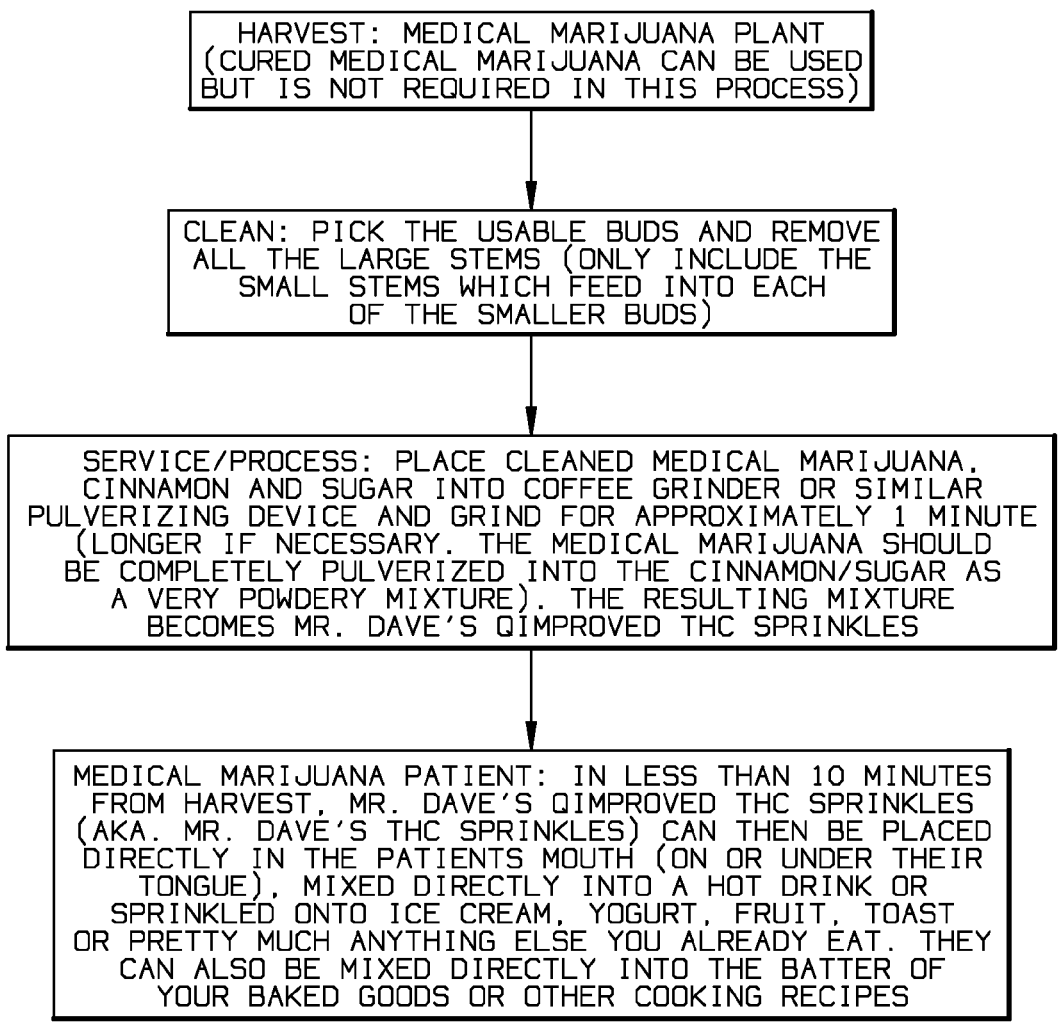

METHODS FOR PREPARING CANNABIS AND RELATED PRODUCTS

BACKGROUND OF THE PRESENT DISCLOSURE

1. Field of the Present Disclosure

The present disclosure is directed to methods for preparing cannabis (hereinafter referred to as "medical marijuana") and the resulting product.

2. Related Art

Medical marijuana contains a number of related compounds that are effective for treating or relieving symptoms associated with a number of diseases, ailments, and conditions. These compounds are known as cannabinoids and include tetrahydrocannabinol (THC), cannabidiol (CBD), cannabinol (CBN), and cannabichromene (CBC). Cannabinoids can be used to treat Alzheimer's disease, multiple sclerosis, Parkinson's disease, chronic inflammation, and other conditions.

Traditionally, medical marijuana has been consumed by inhalation of combustion products (i.e. smoking) or by transferring cannabinoids into oils (e.g. cooking, pharmaceutical preparations). These methods are inefficient, as only a small portion of the cannabinoids reach biological receptors within the user's body. Smoking and cooking may present the user with unpleasant tastes or smells. Pharmaceutical preparations of purified THC can produce overwhelming psychoactive effects while missing the beneficial effects of other cannabinoids.

SUMMARY OF THE PRESENT DISCLOSURE

The present disclosure allows to be prepared for consumption in an efficient process that results in a product having a pleasant taste and smell, which results in a significant increase in efficacy and other advantages apparent from the discussion herein.

According to one aspect of the present disclosure, a method for preparing medical marijuana includes placing prepared medical marijuana in a pulverizing device, placing an alkaline substance in the pulverizing device, and activating the pulverizing device to produce a mixture.

According to another aspect of the present disclosure, a mixture includes prepared medical marijuana and an alkaline substance. The prepared medical marijuana includes medical marijuana buds. The mixture includes from substantially 2 parts to substantially 3 parts of the alkaline substance for every substantially 1 part of the prepared medical marijuana.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings:

FIG. 1 shows a block diagram of an exemplary process for preparing medical marijuana, according to an aspect of the present disclosure.

DETAILED DESCRIPTION OF THE PRESENT DISCLOSURE

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

According to an aspect of the present disclosure, medical marijuana may be prepared by first harvesting the medical marijuana plant and picking the usable buds from the large stems. Small stems connected to the buds may be retained, but the large stems may be discarded. The medical marijuana may be cured after harvesting, but curing is not necessary.

The buds and (optionally) small stems may be placed in a pulverizing device with an alkaline substance, such as, e.g., plant, herb, spice, or other compound. For example, the alkaline substance may be coconut shavings (or another form of coconut) or ground cinnamon. The pulverizing device may be, for example, a coffee grinder, a food processor, a blender, or the like. A sweetener, such as sugar or stevia, may optionally be placed in the pulverizing device as well. Combining the medical marijuana and cannabinoids, which may be acidic, with an alkaline substance may result in a mixture with a more neutral pH. The more neutral pH of the mixture may make the cannabinoids or other compounds more available to the body (i.e. increased bioavailability). The more neutral pH of the mixture may also neutralize acidic compounds in a patient's body, affect the overall pH of the patient, or provide other health benefits.

According to an aspect of the present disclosure, the ratio between these ingredients may be 1 part medical marijuana, 2-3 parts alkaline substance, and 2-3 parts sweetener, with the total being six parts. In other words, an exemplary formulation may be 1 part medical marijuana, 2 parts alkaline substance, and 3 parts sweetener. Another exemplary formulation may be 1 part medical marijuana, 3 parts alkaline substance, and 2 parts sweetener. These ratios are approximate such that each ingredient may vary from the above ratios by as much as 0.1 parts without departing from the spirit and scope of the present disclosure.

Once the ingredients are in place, the pulverizing device may be activated until the ingredients are thoroughly pulverized and combined into a powdery or crystalline mixture.

Pulverizing may be completed in as little as one minute, although longer or shorter times may be necessary depending on the particular ingredients used and the desired characteristics of the resulting mixture.

The resulting mixture may be consumed in a number of ways. For example, the mixture may be consumed by placing it directly in the patient's mouth, on the tongue, under the tongue, or both. The mixture may be added to or sprinkled on foods or drinks, such as coffee, hot chocolate, ice cream, yogurt, fruit, toast, or the like. The mixture may also be incorporated into recipes for baked goods, such as, e.g., brownies, cakes, pie, bread, and the like, as well as other foods. The mixture may also be stored in any suitable way. For example, the mixture may be placed in a sealed glass jar and stored in a cool, dry environment away from direct sunlight.

Prior to consuming or storing the mixture, the mixture may be outgassed to extract any THC from the mixture. Outgassing or removing the THC may result in a mixture with reduced or substantially eliminated psychoactive effects while still possessing at least a portion of the health benefits associated with the original mixture. Outgassing may be accomplished by, for example, heating the mixture to 220° to 240° F. for 20-40 minutes. The time, temperature, and other variables of the outgassing process may be adjusted as needed for the particular properties of the mixture being treated, as well as for achieving a particular result or outcome, without departing from the spirit and scope of the present disclosure.

Outgassing may be accomplished by placing the mixture in an enclosed heating chamber with a constant or regular airflow. The constant airflow may be affected by convention, mechanical means, or other suitable mechanism. A supplemental airflow passage may be connected to the exhaust of the enclosed chamber, and this passage may be used by a patient to inhale the vapor of the outgassing process. This may allow a patient to receive the benefits of the outgassed products while avoiding any effects associated with the outgassed mixture.

The mixture, whether outgassed or not, may contain a more regular or standardized dose of cannabinoids than found in unprocessed medical marijuana. Accordingly, a patient may be able to better regulate his dose by employing one or more aspects of the present disclosure. For example, the effectiveness of the mixture may be affected by the patient's body mass, the patient's tolerance level, and the amount of food and/or drink the patient is consuming along with the mixture. By adjusting or targeting a dose of the mixture based on these factors, the patient may be able to achieve consistent effects regardless of external factors or considerations, such as the strain or type of medical marijuana used, or the patient's consumption of food.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A method of preparing and administering medical marijuana to a human in need thereof consisting essentially of placing marijuana buds, cinnamon, coconut, and a sweetener selected from the group consisting of sugar and stevia into a pulverizing device to produce a medical marijuana mixture, outgassing the medical marijuana mixture by placing the mixture in an enclosed heating chamber with a constant or regular airflow at a temperature of 220° to 240° F. for 20-40 minutes to produce a vapor of outgassing medical marijuana, then connecting an air flow passage to the exhaust of the enclosed heating chamber so that the human can inhale the vapor of the outgassing mixture medical marijuana.

2. A method of preparing and administering medical marijuana to a human in need thereof consisting essentially of placing marijuana buds, cinnamon, coconut, and a sweetener selected from the group consisting of sugar and stevia into a pulverizing device to produce a medical marijuana mixture, outgassing the medical marijuana mixture by placing the mixture in an enclosed heating chamber with a constant or regular airflow at a temperature of 220° to 240° F. for 20-40 minutes to produce a vapor of outgassing medical marijuana, then the human ingesting the outgassed medical marijuana mixture.

* * * * *